United States Patent [19]

Ishikawa

[11] Patent Number: 4,542,238
[45] Date of Patent: Sep. 17, 1985

[54] OPTICALLY ACTIVE SUBSTANCE

[75] Inventor: Nobuo Ishikawa, Yokohama, Japan

[73] Assignee: Daikin Kogyo Co., Ltd., Osaka, Japan

[21] Appl. No.: 665,501

[22] Filed: Oct. 29, 1984

Related U.S. Application Data

[63] Continuation of Ser. No. 424,178, Sep. 27, 1982, abandoned.

[30] Foreign Application Priority Data

Sep. 30, 1981 [JP] Japan .................. 56-1554401

[51] Int. Cl.$^4$ .............................................. C07C 59/00
[52] U.S. Cl. ................................ 562/586; 260/544 F; 260/544 Y
[58] Field of Search .................. 260/544 F, 544 Y; 562/586

[56] References Cited

U.S. PATENT DOCUMENTS 3,250,808  5/1966  Moore et al. .................. 562/586

FOREIGN PATENT DOCUMENTS 707359  4/1965  Canada .................. 562/586
998978  7/1965  United Kingdom .................. 562/586

OTHER PUBLICATIONS

H. Kawa and Nobuo Ishikawa, *Optically Active Perfluoro-2-Propoxypropionic Acid*, Chemistry Letters, pp. 843–846, 1980.

*Primary Examiner*—Paul J. Killos
*Attorney, Agent, or Firm*—Armstrong, Nikaido, Marmelstein & Kubovcik

[57] ABSTRACT

An optically active substance consisting of perfluoro-2-alkoxy carboxylic acid or its derivative represented by the following general formula:

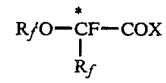

where $R_f$ and $R_f'$ are the same or different perfluoroaliphatic groups, X is a halogen or hydroxyl group, and $\overset{*}{C}$ is a chiral carbon atom, the above carboxylic acid or its derivative being useful for an analytical reagent for optically active compounds, such as a chiral derivatizing agent for the $^{19}F$ NMR or gas chromatographic analysis.

16 Claims, No Drawings

OPTICALLY ACTIVE SUBSTANCE

This application is a continuation of application Ser. No. 424,178 filed Sept. 27, 1982, now abandoned.

BACKGROUND OF THE INVENTION

1. Field of the Invention

The present invention relates to an optically active substance, particularly useful for an analytical reagent for optically active compounds, such as chiral derivatizing agent.

2. Description of the Prior Art

It is well-known that hexafluoro-1,2-epoxypropane (hereinafter referred to "HFPO") differs from the ordinary epoxy compound in that the nucleophilic reagent attacks it primarily at its 2-position carbon.

Particularly noticing that perfluoro-2-alkoxypropionic acid or derivative thereof as produced by a reaction between HFPO and perfluoroalkoxide ion is a compound having an asymmetric carbon at the 2-position and exhibiting superior volatility, the present inventors have thus studied this compound for use as a chiral derivatizing agent in the gas chromatographic or $^{19}$F nmr analysis for chiral compounds.

Among others, the fluoride or chloride of the above perfluoro-2-alkoxypropionic acid was found particularly suitable as a chiral derivatizing agent that exhibits superior volatility and chemical stability.

The present invention is based on novel and useful discoveries as mentioned above.

OBJECTS AND SUMMARY OF THE INVENTION

Accordingly, an object of the present invention is to provide an analytical reagent for optically active compounds, such as a chiral derivatizing agent that exhibits superior volatility and chemical stability.

Another object of the present invention is to provide a chiral derivatizing agent that can be synthesized easily at high yield and yet at low cost.

These and other objects of the invention are achieved in terms of an optically active substance consisting of perfluoro-2-alkoxy carboxylic acid or its derivative represented by the following general formula:

$$R_f'O-\overset{*}{C}F-COX$$
$$|$$
$$R_f$$

where $R_f$ and $R_f'$ are same or different perfluoroaliphatic groups, X a halogen such as a fluorine or chlorine atom, or hydroxyl group, and $\overset{*}{C}$ a chiral carbon atom.

DESCRIPTION OF THE PREFERRED EMBODIMENT

A chiral reagent embodying the present invention is described by way of example with reference to its synthetic method.

For example, if HFPO and hexafluoroacetone are used as raw materials, the reaction that proceeds is expressed by the following formula:

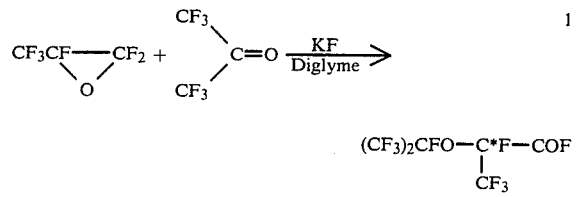

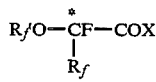

A perfluoro-2-alkoxyalkanoic acid fluoride, namely, perfluoro-2-isopropoxypropionic acid fluoride 1 can thus be obtained in pure form at high yield, for example, of 93%. As the reaction solvent, for example, diglyme (diethylene glycol dimethyl ether) can be used as in the above example.

According to the above synthetic method, use of a catalytic amount of potassium fluoride gives the target fluoride at an unexpectedly high yield of 90% or over in a reaction that proceeds at a temperature equivalent to or lower than room temperature and under reduced pressure. From industrial point of view, therefore, this method provides a process having remarkable merits particularly in yield, process control and cost.

The above synthetic method requires only a catalytic amount of potassium fluoride and specifically 1/10 to 1/20 mol per mol of perfluoroketone. An amount of potassium fluoride that exceeds the above range is not preferable since it oligomerizes the groups $R_f$ and $R_f'$ in the above structural formula and thereby lowers the yield of target compound. Further, an amount of perfluoroketone that is slightly in excess of the above epoxy compound is enough for the reaction. On the other hand, the reaction proceeds satisfactorily even at a temperature not highter than room temperature and under a low pressure, for example, not higher than 5 to 6 kg/cm$^2$.

The acid fluoride that is synthesized by the above method readily hydrolizes to a carboxylic acid, which can further be converted into a salt under presence of a base. The above acid fluoride or salt, for example, of alkali metal forms fluorovinyl ether when it undergoes decarboxylation. This fluorovinyl ether can be a useful constituent monomer of fluoropolymer.

For the group $R_f$ of the reagent embodying the present invention, a perfluoroalkyl group, such as perfluoromethyl, -ethyl, -propyl, -isopropyl, -butyl, or -isobutyl group, or a perfluoroalkenyl group with an additional carbon-carbon double bond to the above perfluoroalkyl group may be used. Particularly, a perfluoroalkyl or -alkenyl group having 6 or less carbon atoms is preferable. On the other hand, the two groups $R_f$ and $R_f'$ may be the same or they may differ from each other. Also for the $R_f'$ group, a perfluoroalkyl group, such as perfluoromethyl, -ethyl, -propyl, -isopropyl, -butyl, and -isobutyl group, and perfluoroalkenyl groups with an additional carbon-carbon double bond to the above perfluoroalkyl group may be used. Particularly, a perfluoroalkyl or -alkenyl group having 12 or less carbon atoms is preferable. It is noted that in consideration of the racemic resolution as mentioned later it is most preferable to use a compound whose $R_f'$ is perfluoro isopropyl or perfluoro n-propyl group and whose $R_f$ is perfluoromethyl group.

The chiral reagent embodying the present invention, for example, perfluoro-2-alkoxyalkanoic acid fluoride is very useful as such.

First, The present inventors have discovered the following experimental fact.

2-alkoxy-2,3,3,3-tetrafluoropropionic acid 2 or a compound as expressed by a formula:

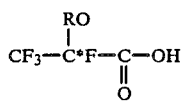

was synthesized by a reaction between HFPO and an alcohol, which then underwent a condensation reaction with α-phenylethylamine. There was thus obtained a mixture of diasteromers as expressed by the following formula:

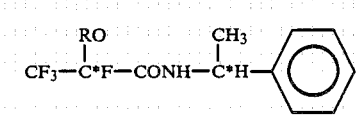

These diasteromers were separated from each other by gas chromatography.

Table 1 shows results of such gas chromatographic separation. Particularly in case of R=isopropyl group, there was shown a high separation performance.

TABLE 1

| R— | R.R.T.* | | |
|---|---|---|---|
| | $r_1$ | $r_2$ | $\alpha(= r_2/r_1)$ |
| Methyl | 0.351 | 0.378 | 1.077 |
| Ethyl | 0.363 | 0.408 | 1.124 |
| Propyl | 0.471 | 0.536 | 1.138 |
| Isopropyl | 0.338 | 0.403 | 1.192 |
| Buthyl | 0.642 | 0.740 | 1.152 |
| Isobuthyl | 0.549 | 0.634 | 1.155 |

*R.R.T. (Relative corrected Retention Time using n-$C_{23}H_{48}$ as standard.)

Based on the above finding, optically active perfluoro-2-alkoxyalkanoic acid fluorides, particularly perfluoro-2-isopropoxyalkanoic acid fluoride, embodying the present invention were individually reacted with other optically active substances having an active hydrogen atom, for example, primary amines under dehydrofluorination.

Individual diasteromers differed from each other in adsorptive behavior and solubility, so they could be separated or resolved readily by gas chromatography. Separated diastereomers could be individually hydrolyzed to obtain an optically resolved perfluoro-2-alkoxyalkanoic acid that could be used as a chiral reagent.

For example, a diasteromer 3 was derived by a dehydrofluorination/condensation reaction as expressed by the following formula:

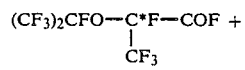

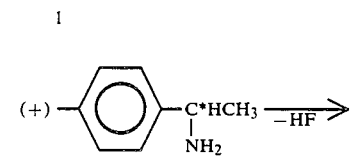

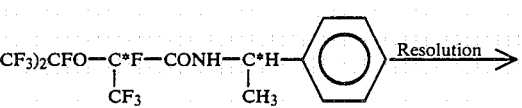

$$3\begin{cases} a\,(+)\,(-) \\ b\,(-)\,(+) \end{cases}$$

$$4\begin{cases} (+) \\ (-) \end{cases}$$

Table 2 shows the characteristic behavior of an optically active substance thus separated or perfluoro-2-isopropoxypropionic acid 4,

TABLE 2

| | (+)-4 | (−)-4 |
|---|---|---|
| Yield (%) | 58 | 56 |
| Boiling point (°C./mm Hg) | 76–77/40 | |
| $[\alpha]_D^{20}$ (pure, l = 1) | +31.10° | −31.32° |
| IR spectra (cm$^{-1}$) | 3200 (OH) | 1780 (C=O) |
| $^1$H NMR (CDCl$_3$) | δ10.5 | |
| $^{19}$F NMR* (pure) | 3.5 (3F), 4.2 (3F), 6.0 (3F) | |
| | 51.6 (1F), 67.0 (1F) | |

*δ ppm upfield from ext. CF$_3$CO$_2$H

Further, an acid chloride (+)-5 was derived from (+) -4 as separated above using phosphorus pentachloride, which was then reacted with a partially resolved arylalkylamine to produce diastereomers 6. These diastereomers were subjected to gas chromatography. Table 3 shows the results.

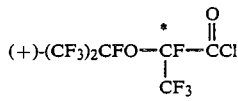

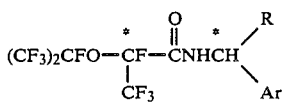

TABLE 3

| R— | Ar— | Column temp. °C. | R.T.* (min) r (−) | r (+) | $\alpha =$ r(+)/r(−) |
|---|---|---|---|---|---|
| CH$_3$— | phenyl | 90 | 9.62 | 10.95 | 1.138 |
| C$_2$H$_5$— | phenyl | 90 | 14.66 | 16.53 | 1.128 |
| (CH$_3$)CH— | phenyl | 90 | 18.30 | 21.38 | 1.168 |
| CH$_3$— | CH$_3$-phenyl | 90 | 17.40 | 20.46 | 1.176 |
| CH$_3$— | Cl-phenyl | 120 | 5.80 | 6.62 | 1.141 |

TABLE 3-continued

| R— | Ar— | Column temp. °C. | R.T.* (min) r (−) | r (+) | α = r(+)/r(−) |
|---|---|---|---|---|---|
| CH$_3$— | Br—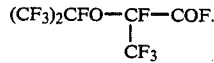— | 120 | 9.02 | 10.37 | 1.150 |
| CH$_3$— | 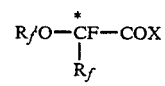 | 140 | 9.98 | 11.45 | 1.147 |

*R.T. (uncorrected Retention Time)

The above results show that in every case excellent resolution could be achieved under very moderate analytical condition. Further, there was made an interesting finding that when (+) -5 was used the first peak always corresponded to the (−)-enantiomer.

The invention will be understood more readily by reference to the following example, though variations may be made by one skilled in the art without departing from the spirit and scope of the invention.

EXAMPLE

In a 300 cc reactor pressure tube, 0.6 g (10 mmol) of potassium fluoride roasted dry and 20 ml of diglyme were added. The solution was cooled down to −70° C. and then introduced into 17.76 g (107 mmol) of hexafluoroacetone that was liquefied beforehand. After being allowed to slowly recover the room temperature fully, the mixture was agitated for an hour. A uniform reaction solution was thus formed, which was then again cooled down to −70° C. and then introduced into 15.77 g (95 mmol) of hexafluoro-1,2-epoxypropane. The mixture was allowed to recover the room temperature and it was then agitated for an hour. A gaseous product, as generated under reduced pressure of 20 mmHg, was trapped by a dry ice-acetone bath. The $^{19}$F NMR measurement identified the trapped gas with an almost pure target compound: perfluoro-2-isopropoxypropionic acid fluoride $$(CF_3)_2CFO-\underset{\underset{CF_3}{|}}{CF}-COF.$$

The produced amount of 23.33 g corresponded to a yield of 93% when estimated from the amount of hexafluoro-1,2-epoxypropane. The boiling point of the product was 50° to 52° C./760 mmHg.

It was found that the diglyme solution after separation of the product could be reused for the same reaction. For example, when the remaining solution was cooled at −70° C. and 31.87 g (192 mmol) of hexafluoroacetone and 29.88 g (180 mmol) of hexafluoro-1,2-epoxypropane were introduced in it in a similar manner to the above for a 1-hour reaction, 56.17 g of the target compound was obtained (yield: 94%).

Next, 3.63 g (30 mmol, $\alpha_D^{25}+37.45°$) of (+)-α-phenethylamine and 3.03 g (30 mmol) of triethylamine were mixed in 20 ml of acetonitrile. 9.96 g (30 mmol) of the above (±)-perfluoro-2-isopropoxypropionic acid fluoride was added dropwise to the mixture. After completion of the dropwise addition, the reaction solution was allowed to recover the room temperature and it was then agitated for another 30 min. The reaction mixture was poured into water and the oily layer was subjected to extraction with ethyl ether. The ether extracts were washed successively with 1N hydrochloric acid, 5% aqueous sodium bicarbonate, and saturated sodium chloride solution and then dried over magnesium sulfate. As ether was removed under reduced pressure, 11.95 g of almost pure diastereomeric amide mixture was obtained (yield: 92%). 3 g of this diasteromer mixture was passed with a hexane-benzene mixture (3:1) as solvent through a 1.0 in.φ×20 in. column filled with silica gel approx. 30 times in quantity for separation and purification, which resulted in pure amides. 4.09 g in total of an amide of (+)-(+)-form (3a in the above) was thus obtained as the first fraction (yield: 63%). It exhibited a melting point of 49.5° to 50.5° C. and $[\alpha]_D^{20}+74.4°$ (c1.00, CHCl$_3$). Further, 3.77 g of (−)-(+) form (3b in the above) was obtained as the second fraction (yield: 58%). It exhibited a melting point of 75° to 75° C. and $[\alpha]_D^{20}+85.8°$ (c1.00, CHCl$_3$).

2.2 ml of conc. sulfuric acid was added to 1.50 g (3.5 mmol) of the above (+)-(+) amide under icecooled condition. After 1 hour agitation at room temperature, the mixture was poured onto ice and the oily fraction was subjected to extraction with ether. The extracts were concentrated under reduced pressure and 4 ml of 7N aqueous sodium hydroxide was added to residues for heating under refluxed condition. The reaction mixture was made acidic with use of 6N hydrochloric acid and a carboxylic acid that was produced was extracted with ether. After drying over magnesium sulfate, extracts were concentrated and distilled to give 0.96 g of (+)-perfluoro-2-isopropoxypropionic acid (yield: 83%).

It exhibited a boiling point of 76° to 77° C./40 mmHg and $[\alpha]_D^{20}+31.1°$ (pure, l=1). The (−)-enantiomer was similarly prepared, which exhibited $[\alpha]_D^{20}-31.3°$ (pure, l=1).

Optically active isopropoxypropionic acid enantiomers thus separated were reacted with phosphorus pentachloride to give their acid chlorides. They were then reacted with partially resolved arylalkylamines to derive their diasteromers, which were gas chromatographed for successful separation of individual amine enantiomers, each having its own prescribed optical activity.

What is claimed is:

1. An optically active substance consisting of the optically active enantiomer perfluoro-2-alkoxy carboxylic acid or its derivative represented by the following general formula:

$$R_f'O-\overset{*}{\underset{\underset{R_f}{|}}{CF}}-COX$$

where $R_f$ is a perfluoroaliphatic group, $R_f'$ is a perfluoroisopropyl group, a perfluorobutyl group or a perfluoroisobutyl group, X is a halogen or a hydroxyl group, and $\overset{*}{C}$ is a chiral carbon atom.

2. An optically active substance as claimed in claim 1 wherein $R_f$ is selected from a perfluoroalkyl and a perfluoroalkenyl group having no more than 6 carbon atoms.

3. An optically active substance as claimd in claim 1 which is composed of a perfluoro-2-isopropoxypropionic acid fluoride.

4. An optically active substance as claimed in claim 1 which is composed of a carboxylic acid.

5. An optically active substance as claimed in claim 1 which is composed of an acid chloride.

6. An optically active substance as claimed in claim 2 which is composed of a perfluoro-2-isopropoxy-propionic acid fluoride.

7. An optically active substance as claimed in claim 2 which is composed of a carboxylic acid.

8. An optically active substance as claimed in claim 2 which is composed of an acid chloride.

9. An improved method of derivatizing optically active compounds using optically active analytical reagents wherein the improvement comprises the use of an optically active substance consisting of the enantiomer of perfluoro-2-alkoxy carboxylic acid or its derivatives represented by the following general formula:

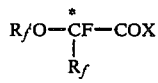

wherein $R_f$ is a perfluoroaliphatic group, $R_f'$ is a perfluoroisopropyl group, a perfluorobutyl group or a perfluoroisobutyl group, X is halogen or a hydroxyl group and $\overset{*}{C}$ is a chiral carbon atom as the analytical reagent.

10. A derivatization method as claimed in claim 9 wherein $R_f$ of the analytical reagent is a perfluoroalkyl and/or perfluoroalkenyl group having no more than 6 carbon atoms.

11. A derivatization method as claimed in claim 9 in which the analytical reagent is composed of a perfluoro-2-isopropoxy-propionic acid fluoride.

12. A derivatization method as claimed in claim 9 in which the analytical reagent is composed of a carboxylic acid.

13. A derivatization method as claimed in claim 9 in which the analytical reagent is composed of an acid chloride.

14. A derivatization method as claimed in claim 10 in which the analytical reagent is composed of a perfluoro-2-isopropoxy-propionic acid fluoride.

15. A derivatization method as claimed in claim 10 in which the analytical reagent is composed of a carboxylic acid.

16. A derivatization method as claimed in claim 10 in which the analytical reagent is composed of an acid chloride.

* * * * *

UNITED STATES PATENT AND TRADEMARK OFFICE
CERTIFICATE OF CORRECTION

PATENT NO. : 4,542,238
DATED : September 17, 1985
INVENTOR(S) : NOBUO ISHIKAWA

It is certified that error appears in the above-identified patent and that said Letters Patent is hereby corrected as shown below:

On the cover page, Item [30], change "56-1554401" to --- 56-155440 ---.

Signed and Sealed this

Third Day of June 1986

[SEAL]

Attest:

DONALD J. QUIGG

Attesting Officer

Commissioner of Patents and Trademarks